(12) United States Patent
Kanauchi et al.

(10) Patent No.: US 6,413,378 B1
(45) Date of Patent: Jul. 2, 2002

(54) APPARATUS FOR SEPARATION AND PURIFICATION OF SATURATED HYDROCARBON AND METHOD FOR SEPARATION AND PURIFICATION

(75) Inventors: Masanobu Kanauchi; Yasuhiko Arimori, both of Tokyo; Toshihiro Nakano, Yamaguchi-ken, all of (JP)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/647,789

(22) PCT Filed: Apr. 6, 1999

(86) PCT No.: PCT/JP99/01812
§ 371 (c)(1),
(2), (4) Date: Oct. 5, 2000

(87) PCT Pub. No.: WO99/51552
PCT Pub. Date: Oct. 14, 1999

(30) Foreign Application Priority Data

Apr. 7, 1998 (JP) ............................. 10-111489
Aug. 28, 1998 (JP) ............................. 10-243562

(51) Int. Cl.$^7$ ............................. B01D 3/40; B01D 3/42

(52) U.S. Cl. ............................. 203/1; 196/99; 196/100; 196/106; 196/132; 196/141; 202/154; 202/155; 202/160; 202/172; 203/2; 203/3; 203/78; 203/84; 203/98; 203/DIG. 18; 208/348; 208/350; 208/364; 208/DIG. 1; 585/809; 585/956

(58) Field of Search ............................. 203/1–3, 2, 50, 203/78, DIG. 18, 98, 84; 202/160, 206, 154, 155, 172; 585/809, 810, 956; 196/132, 99, 100, 106, 141; 208/350, 348, 364, DIG. 1

(56) References Cited

U.S. PATENT DOCUMENTS 4,053,369 A * 10/1977 Cines ........................... 203/52
4,057,995 A * 11/1977 Kleiss ........................... 203/1
4,419,188 A * 12/1983 McCall ........................ 203/98

FOREIGN PATENT DOCUMENTS

| JP | 51-127006 | 11/1976 |
|----|-----------|---------|
| JP | 56-83421 | 7/1981 |
| JP | 57-54129 | 3/1982 |
| JP | 57-75104 | 5/1982 |
| JP | 60-54704 | 3/1985 |
| JP | 60-104021 | 6/1985 |
| JP | 60-156623 | 8/1985 |

* cited by examiner

Primary Examiner—Virginia Manoharan
(74) Attorney, Agent, or Firm—Armstrong, Westerman & Hattori, LLP

(57) ABSTRACT

An extractive distillation tower 4 supplied with a feedstock containing butadiene and a solvent and for distilling the feedstock to separate and purify the butadiene. The tower 4 includes sensors 32, 34 for detecting concentrations of specific impurities other than butadiene; a sensor for detecting a concentration of the butadiene; a sensor 30 for detecting a differential pressure between the top and bottom of the tower 4; a valve 48 for controlling the flow rate of part of fluid taken out from a bottom of the tower 4 and returned to the tower 4; a valve 23 for controlling a ratio of a solvent fed to the tower 4; a reflux ratio valve 28 for controlling the flow rate of part of remaining component of the feedstock taken out from a top of the tower 4 and refluxed; a heater 36 for controlling a bottom temperature of the tower 4; and a predictive control 60 for calculating forecasted values of the concentrations of the specific impurity and the butadiene after a time based on these sensors and controlling the system based on the forecasted values.

14 Claims, 5 Drawing Sheets

FIG. 4

* DIRECTION OF CONTROL OF MV WHEN DESIRING TO LOWER CV

| MV/DV<br>CV | MV1<br>50<br>RETURN RATIO | MV2<br>23<br>SOLVENT RATIO | MV3<br>28<br>REFLUX RATIO | MV4<br>36<br>BOTTOM TEMPERATURE |
|---|---|---|---|---|
| CV1 (FCV1)<br>32<br>7TH STAGE CIS-2-BUTEN | ← | → | → | ← |
| CV2 (FCV2)<br>34<br>7TH STAGE TRANS-2-BUTEN | ← | → | → | ← |
| CV3 (FCV3)<br>25<br>TOP BD | → | ← | ← | → |
| CV4 (FCV4)<br>30<br>TOP-BOTTOM DIFFERENTIAL PRESSURE | → | ← | → | → |

APPARATUS FOR SEPARATION AND PURIFICATION OF SATURATED HYDROCARBON AND METHOD FOR SEPARATION AND PURIFICATION

TECHNICAL FIELD

The present invention relates to an apparatus and method for separation and purification of unsaturated hydrocarbons, more particularly relates to an apparatus and method for separation and purification of unsaturated hydrocarbons which enable a target unsaturated hydrocarbon to be taken out stably at a predetermined concentration.

BACKGROUND ART 1,3-butadiene, isoprene, and other conjugated dienes are generally separated and purified as unsaturated hydrocarbons by extractive distillation using an extraction solvent from a $C_4$ fraction or $C_5$ fraction obtained by cracking naphtha and separating the ethylene, propylene, and other $C_2$ and $C_3$ hydrocarbons (Japanese Examined Patent Publication (Kokoku) No. 45-17405, Japanese Examined Patent Publication (Kokoku) No. 45-17411, Japanese Examined Patent Publication (Kokoku) No. 47-41323, Japanese Unexamined Patent Publication (Kokai) No. 56-83421, etc.)

Normally, this extractive distillation is performed using an apparatus comprised of an extractive distillation tower and stripping tower. Conjugated dienes, which dissolve relatively easily in the solvents included in the $C_4$ fraction or $C_5$ fraction, are taken out as mixtures with the solvents from the bottom of the extractive distillation tower and sent to the stripping tower, where the conjugated dienes and solvents are separated. The solvents are then returned to the extractive distillation tower.

In the conventional separation and purification apparatus and method for conjugated dienes, the general practice has been to control the ratio of the extraction solvent fed to the extractive distillation tower, control the flow rate of part of the residual components of the feedstock taken out from the top of the extractive distillation tower (residuum of feedstock after conjugated dienes have been extracted) and reflux it to the extractive distillation tower, control the bottom temperature of the extractive distillation tower, etc. to separate and purify a stable quality of conjugated dienes.

With such a conventional separation and purification apparatus and method of conjugated dienes, however, when the composition of the feedstock fed to the extractive distillation tower varied, the concentration of the target conjugated dienes taken out from the tower varied. Consequently, it was difficult to take out a stable quality of conjugated dienes.

Note that to take out an extract of a high concentration and constant concentration of conjugated dienes from the extractive distillation tower, it is preferable to return the extract taken out from the bottom of the extractive distillation tower to the extractive distillation tower and control the return ratio. If the return ratio to the extractive distillation tower, however, is not allowed to fluctuate in accordance with the ratio of the extraction solvent, the bottom temperature, the bottom pressure, the ratio of the feedstock fed, the concentration of the conjugated dienes in the feedstock, etc., it is not possible to maintain a constant concentration of the target butadiene, isoprene, or other conjugated dienes and concentration of other specific impurities in the extractive distillation tower. Further, it is close to impossible for an operator to manually handle this control procedure. Therefore, at the present time, priority is given to ease of operation even if allowing the concentration of the conjugated dienes taken out from the extractive distillation tower to fluctuate somewhat. The return ratio is not controlled, but the flow rate to the next process is controlled and the surplus is returned. Therefore, there was a large fluctuation in the conjugated dienes taken out from the extractive distillation tower. In particular, if there is a large fluctuation in concentration of the conjugated dienes taken out in the first extractive distillation tower used for the separation and purification apparatus of the conjugated dienes, increasing the purity of the conjugated dienes in the subsequent processes becomes difficult and stably obtaining high purity conjugated dienes becomes difficult.

DISCLOSURE OF THE INVENTION

An object of the present invention is to provide an apparatus and method for separation and purification of unsaturated hydrocarbons which enable a target conjugated diene or other unsaturated hydrocarbons to be stably taken out at a predetermined concentration regardless of variations in the components of the feedstock or fluctuations in the ratio of the feedstock fed.

To achieve this object, the apparatus for separation and purification apparatus of an unsaturated hydrocarbon of the present invention comprises an extractive distillation tower fed with feedstock containing unsaturated hydrocarbons and a solvent and distilling the feedstock to separate and purify a target unsaturated hydrocarbon; an impurity concentration detecting means for detecting a concentration of a specific impurity other than the target unsaturated hydrocarbon at the extractive distillation tower or another tower connected to the extractive distillation tower (the extractive distillation tower, etc.); a target material concentration detecting means for detecting a concentration of the target unsaturated hydrocarbon at the extractive distillation tower or another tower connected to the extractive distillation tower; a return ratio control means for controlling a flow rate of part of a fluid including the target unsaturated hydrocarbon taken out from a bottom of the extractive distillation tower and returned to the extractive distillation tower; a solvent ratio control means for controlling a ratio of the solvent fed to the extractive distillation tower; a reflux ratio control means for controlling a flow rate of part of a residual component of the feedstock taken out from a top of the extractive distillation tower (meaning the residuum of the feedstock after the unsaturated hydrocarbons has been extracted, but also including some unsaturated hydrocarbons, same below) and refluxed to the extractive distillation tower; a bottom temperature control means for controlling a bottom temperature of the extractive distillation tower; and a predictive control means for calculating forecasted values of the concentration of the specific impurity and the concentration of the target unsaturated hydrocarbon after a predetermined time based on values detected by the impurity concentration detecting means and target material concentration detecting means and controlling the return ratio control means, solvent ratio control means, reflux ratio control means, and bottom temperature control means based on the forecasted values.

Further, the method for separation and purification of an unsaturated hydrocarbon according to the present invention comprises the steps of feeding a feedstock containing a target unsaturated hydrocarbon and a solvent to an extractive distillation tower; detecting a concentration of a specific impurity other than the target unsaturated hydrocarbon at the extractive distillation tower or another tower connected to the extractive distillation tower; detecting a concentration of the target unsaturated hydrocarbon at the extractive distillation tower or another tower connected to the extractive distillation tower; controlling a return flow rate of part of a fluid containing the target unsaturated hydrocarbon taken out from a bottom of the extractive distillation tower and returned to the extractive distillation tower; controlling a ratio of the solvent fed to the extractive distillation tower; controlling a reflux flow rate of part of a residual component of the feedstock taken out from a top of the extractive distillation tower and refluxed to the extractive distillation tower; controlling a bottom temperature of the extractive distillation tower; and calculating forecasted values of the concentration of the specific impurity and the concentration of the target unsaturated hydrocarbon after a predetermined time based on values detected by the impurity concentration detecting step and target material concentration detecting step and controlling the return flow rate, the ratio of the solvent, the reflux flow rate, and the bottom temperature based on the forecasted values.

The solvent used in the present invention may be dimethylformamide, diethylformamide, dimethylacetomide, and other N-alkyl substituted lower fatty acid amides, furfural, N-methylpyrrolidone, formylmorpholine, β-methoxypropionitrile, and other solvents used for extractive distillation of diolefins from hydrocarbon fractions for example. These solvents may be used alone or may be used in mixtures of two or more types. Further, to adjust the boiling point, suitable amounts of water, methanol, etc. may be mixed. Further, it is also possible to jointly use polymerization inhibitors to inhibit polymerization of the diolefins and acetylenes, antioxidants, defoaming agents, etc.

The extraction medium (solvent) is preferably fed to the extractive distillation tower from an extractive distillation medium feed means provided at a position higher than the position feeding the petroleum fraction containing the unsaturated hydrocarbons in the extractive distillation tower (petroleum fraction feed means).

Further, the polymerization inhibitor may be continuously fed from a position higher than the feed position of the extraction medium. As the position higher than the extraction medium feed position, for example, mention may be made of the side of the extractive distillation tower higher than the extraction medium feed position or the inlet or outlet of the condenser of the top of the extractive distillation tower. Among these, provision at the inlet of the top condenser is preferable in that it enables the production of polymers inside the condenser to be suppressed and enables the production of polymers even in processes after the separator to be suppressed. The polymerization inhibitor is preferably one which stops or suppresses polymerization by a chain transfer reaction, in particular, a lower alkylhydroxylamine.

The feedstock (petroleum fraction) used in the present invention contains unsaturated hydrocarbons. The petroleum fraction normally is obtained by cracking naphtha. As the petroleum fraction, there are for example a $C_2$ fraction containing mainly $C_2$ hydrocarbons, a $C_3$ fraction containing mainly $C_3$ hydrocarbons, a $C_4$ fraction containing mainly $C_4$ hydrocarbons, and a $C_5$ fraction containing mainly $C_5$ hydrocarbons. Among these, a fraction increased in the concentration of the unsaturated hydrocarbons due to the extractive distillation etc. is preferred. Further, a fraction containing a large amount of conjugated dienes as unsaturated hydrocarbons is preferred. In particular, a $C_4$ fraction containing a large amount of butadiene or a $C_5$ fraction containing a large amount of isoprene is preferred.

The apparatus and method of the present invention are effective when applied to the case of trying to obtain a concentration of an unsaturated hydrocarbon in the petroleum fraction of normally at least 90 percent, preferably at least 95 percent (specifically, extracting and distilling the petroleum fraction to increase the concentration of the unsaturated hydrocarbon).

According to the apparatus and method of the present invention, it is possible to stably take out a target unsaturated hydrocarbon at a predetermined concentration regardless of variations in the feedstock components.

BRIEF DESCRIPTION OF THE DRAWINGS

The present invention will be described below with reference to embodiments shown in the drawings.

FIG. 4 is a graph of the relationship of the measurement data and control parameters.

BEST MODE FOR CARRYING OUT THE INVENTION

First Embodiment

In the present embodiment, the explanation will be given of the process of separation and purification of conjugated dienes from a $C_4$ fraction or $C_5$ fraction containing conjugated dienes as unsaturated hydrocarbons.

Figure 1:
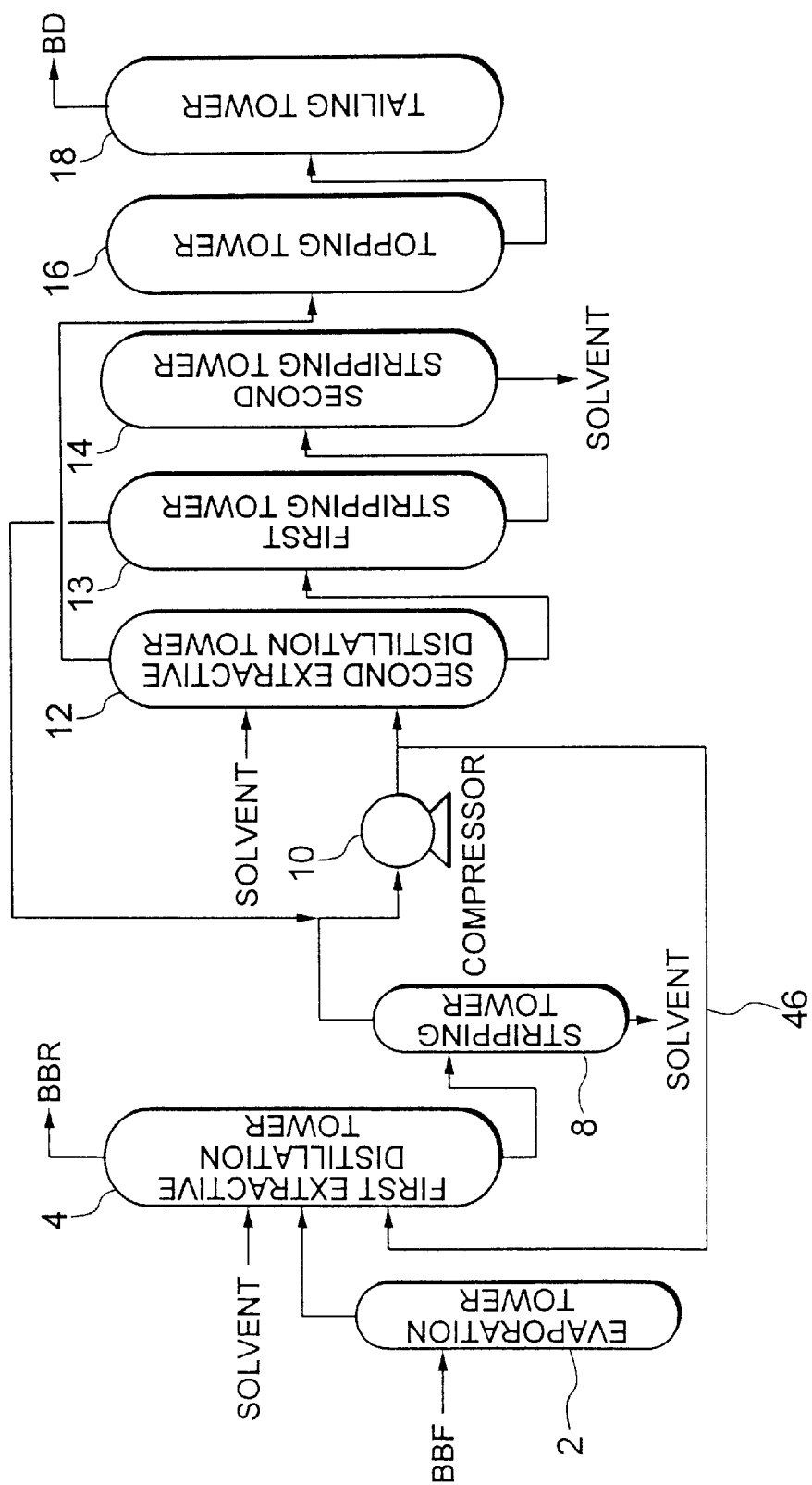
FIG. 1 is a schematic view of the overall configuration of a separation and purification apparatus for conjugated dienes.

As shown in FIG. 1, the $C_4$ fraction or $C_5$ fraction is first vaporized at an evaporation tower 2 and fed to a first extractive distillation tower 4. Further, the solvent is fed to a stage higher than the $C_4$ fraction or $C_5$ fraction feed position of the first extractive distillation tower 4. The solvent containing the conjugated dienes is fed from the bottom of the first extractive distillation tower 4 to a position several stages down from the top of a stripping tower 8. In the tower, the conjugated dienes and solvent are separated. The bottom temperature of the tower is normally controlled to become the boiling point of the solvent at a tower pressure of 0.5 to 5 atm. The conjugated dienes are taken out from the top of the stripping tower 8. Part is sent to a second extractive distillation tower 12 where it is purified, while the remainder is returned to the first extractive distillation tower 4. Solvent of normally 100 to 200° C. is taken out from the bottom of the stripping tower 8.

In the present embodiment, by detecting the change in the concentration of the impurity near the bottom of the first extractive distillation tower and the change of the concentration of the conjugated dienes in the gas discharged from the top of the first extractive distillation tower and controlling the ratio of the solvent fed to the first extractive distillation tower 4, controlling the return ratio from the stripping tower 8 to the first extractive distillation tower 4, controlling the reflux ratio at the top of the first extractive distillation tower 4, and controlling the bottom temperature of the first extractive distillation tower 4 in accordance with these changes, it is possible to extract a constant concentration of conjugated dienes.

Below, a detailed explanation will be given of the process of separation and purification of butadiene from a $C_4$ fraction as an example.

As shown in FIG. 1, a feedstock ($C_4$ component in naphtha) C4F containing butadiene is fed to the evaporation tower 2 where the feedstock C4F is vaporized. In the evaporation tower 2, the C4F is vaporized by holding the tower temperature at preferably 20 to 80° C., more preferably 40 to 80° C., and holding the tower pressure at an absolute pressure of preferably 2 to 8 atm, more preferably 4 to 6 atm.

The feedstock C4F vaporized at the evaporation tower 2 is next fed to the first extractive distillation tower 4. The first extractive distillation tower 4 is fed with a solvent together with the vaporized feedstock C4F. The ratio of the solvent fed to the first extractive distillation tower is controlled as explained later, but in general the solvent is fed to 100 to 1000 parts by weight, more preferably 200 to 800 parts by weight, with respect to 100 parts by weight of the feedstock C4F. The temperature of the solvent is preferably low since the solubility is high, but preferably is 10 to 100° C., more preferably 20 to 60° C. since it affects the internal temperature of the first extractive distillation tower 4 or the change of the reflux ratio.

The solvent is not particularly limited so long as it enables dissolution and extraction of butadiene as one example of conjugated dienes, but specifically acetone, methylethylketone, dioxane, isoprene cyclic sulfone, acetonitrile, alcohol, glycol, N-methyloldamine, N-ethylsuccinic acid imide, N-methylpyrrolidone, N-methyl-2-pyrrolidone, hydroxylethylpyrrolidone, N-methyl-5-methylpyrrolidone, furfural, 2-heptenone, dimethylformamide, dimethylacetamide, N,N-dimethylacetone acetic acid amide, morpholine, N-formylmorpholine, N-methylmorpholin-3-one, sulforane, methylcarbitol, tetrahydrofuran, aniline, N-methyloxazolidone, N-methylimidazole, N,N'-dimethylimidazolin-2-one, 1-oxo-1-methylphosphorin, methylcyanoacetate, ethylacetoacetate, ethylacetate, malonic acid dimethylester, propylene carbonate, methylcarbitol, triethyl phosphate, diethylene glycol monomethyl ether, dimethyl sulfoxide, γ-butyrolactone, etc. may be mentioned. In the present embodiment, as the extraction medium, among these, amide compounds, in particular dimethylformamide, are preferable.

The extraction medium is fed to the first extractive distillation tower 4 from an extraction medium feed stage provided at a position higher than the stage feeding the petroleum fraction containing the conjugated dienes (feedstock BBF) in the first extractive distillation tower 4 (petroleum fraction feed stage).

Figure 2:
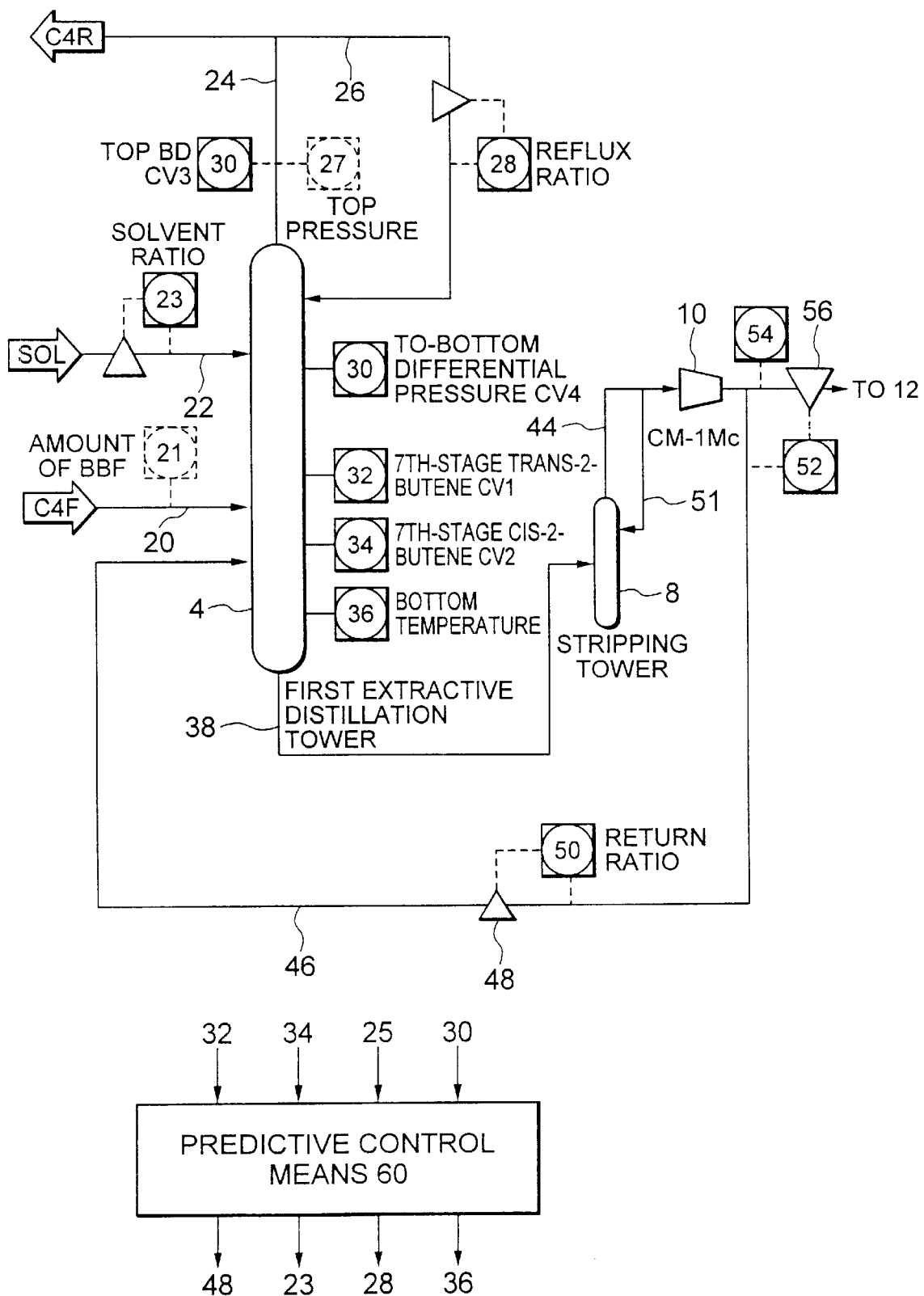
FIG. 2 is a schematic view of a method of control of a first extractive distillation tower shown in FIG. 1.

At the top of the first extractive distillation tower 4 shown in FIGS. 1 and 2, the gas having a volatility (solubility) of at least butadiene is separated, the raffinate C4R of the feedstock C4F from which the butadiene component has been separated is taken out, and a high concentration butadiene extract is taken out from the bottom of the tower by controlling the bottom pressure of the first extractive distillation tower 4 to an absolute pressure of preferably 1 to 10 atm, more preferably 5 to 7 atm, and the bottom temperature to preferably 100 to 160° C., more preferably 110 to 130° C.

The amount of the $C_4$ fraction dissolved in the solvent taken out from the bottom of the first extractive distillation tower 4 is determined by the solvent ratio, temperature, and pressure at the bottom of the tower. Therefore, to take out a constant concentration butadiene extract from the bottom of the first extractive distillation tower 4, it is necessary to control the solvent ratio at the bottom of the first extractive distillation tower 4, the reflux ratio of the top, the bottom temperature, etc. Further, to increase the concentration of the butadiene extract solution taken out from the bottom of the first extractive distillation tower 4, as mentioned later, it is necessary to return the extract taken out from the bottom of the first extractive distillation tower 4 or, in accordance with need, part from which the solvent has been removed through the stripping tower 8, to the first extractive distillation tower 4. In the present embodiment, as explained later, the return ratio of the extract taken out from the bottom of the first extractive distillation tower 4 to the first extractive distillation tower 4 is also controlled.

The C4 raffinate taken out from the top of the first extractive distillation tower 4 is sent to a not shown residual component tank. Part of the residual gas BBR is condensed at a not shown condenser and refluxed by returning it to the top of the first extractive distillation tower 4. The reflux ratio of the residual gas BBR is also controlled as explained later.

At the bottom of the first extractive distillation tower 4 shown in FIGS. 1 and 2, an extract containing a high concentration of the target butadiene is taken out and sent to the stripping tower 8. In the stripping tower 8, the bottom pressure is held at an absolute pressure of 1 to 3 atm and the bottom temperature is held at 150 to 200° C. The solvent is separated from the extract and discharged from the bottom of the tower. At the top of the stripping tower 8, a stripped gas containing a large amount of butadiene from which the solvent has been separated is produced. When condensing part of the stripped gas in the condenser, the condensed part is refluxed by returning it to the top of the stripping tower 8. Part of the uncondensed part is returned through a compressor 10 to the first extractive distillation tower 4, while the remainder is sent to a second extractive distillation tower 12. When condensing all of the stripped gas at the condenser, part of the condensed liquid is refluxed by returning it to the top of the stripping tower 8, part of the remainder is returned through the compressor 10 to the first extractive distillation tower 4, and the rest is sent to the second extractive distillation tower 12. In this way, what is returned to the first extractive distillation tower 4 is vapor in case of handling with C4 fraction, or liquid in case of C5 fraction. In both cases, however, the return ratio is controlled as explained later.

In the second extractive distillation tower 12, impurities having a volatility (solubility) of not more than butadiene are separated from the bottom of the tower. At the top of the tower, gas containing a high concentration of butadiene is taken out by holding the bottom pressure at an absolute pressure of 3 to 6 atm and holding the bottom temperature at 100 to 150° C. An extract containing a large amount of impurities separated from the bottom of the second extractive distillation tower 12 is led to the first stripping tower 13. At the first stripping tower 13, the bottom pressure is held at an absolute pressure of 1 to 3 atm and the bottom temperature is held at 120 to 180° C. The butadiene is separated from the extract and the stripped gas containing the butadiene is returned to the inlet of the condenser of the stripping tower 8. The liquid at the bottom of the second extractive distillation tower 12 is sent to the second stripping tower 14. At the second stripping tower 14, the bottom pressure is held at an absolute pressure of 1 to 3 atm and the bottom temperature is held at 150 to 200° C. The solvent is separated from the extract, exhausted from the bottom of the tower, and reused. The stripped gas is exhausted from the top of the tower.

The distillation gas containing a large amount of butadiene taken out from the top of the second extractive distillation tower 12 is successively sent to a topping tower 16 and a tailing tower 18. At the topping tower 16, the methylacetylene impurity having a lower boiling point than butadiene is removed by making the bottom pressure 3 to 7 atm and making the bottom temperature 30 to 60° C. Further, at the tailing tower 18, the impurities having a higher boiling point than butadiene, for example, cis-2-butene, 1,2-butadiene, and ethylacetylene, are removed by making the bottom pressure 3 to 7 atm and the bottom temperature 40 to 70° C. In the present embodiment, the concentration of the butadiene in the finally obtained extract becomes at least 99 percent.

Next, an explanation will be given of the control apparatus and control method of the first extractive distillation tower 4 according to the present embodiment referring mainly to FIGS. 2 to 4.

As shown in FIG. 4, a feedstock feed line 20 to which a feedstock (petroleum fraction) C4F containing butadiene is fed is connected to an intermediate stage of the first extractive distillation tower 4. The feedstock feed line 20 has a feedstock flowmeter 21 attached to it to measure the flow rate of the feedstock fed to the first extractive distillation tower 4. The feedstock flow rate data measured by the feedstock flowmeter 21 is input to a predictive control means 60. The predictive control means 60 is comprised of a specific electrical circuit having a memory circuit, a general use PC, general use computer, large computer, etc. and stores a program for the later mentioned control. Note that instead of a program for control discussed later, it is also possible to provide a logic circuit operating in that way.

In the first extractive distillation tower 4, a solvent feed line 22 is connected to the top plate side of the feedstock feed line 20 and feeds the solvent for extraction of the butadiene to the inside of the first extractive distillation tower 4. The solvent feed line 22 has a solvent flow rate control valve 23 attached to it. This controls the flow rate to the first extractive distillation tower 4 based on the output signal from the predictive control means 60. The method of control will be explained below.

A residual gas exhaust line 24 is connected to the top of the first extractive distillation tower 4 and exhausts part of the residual gas remaining after extraction of the butadiene from the feedstock in the first extractive distillation tower 4 (however, containing some butadiene) to a not shown residual component tank. A reflux line 26 is also connected to the exhaust line 24 and refluxes part of the residual gas taken out at the exhaust line 24 to the top of the first extractive distillation tower 4.

The exhaust line 24 near the top of the first extractive distillation tower 4 has attached to it a target material concentration sensor 25 for detecting the concentration of butadiene at the top of the tower (target material concentration detecting means) and a top pressure sensor 27 for measuring the pressure inside the top of the tower. As the target material concentration sensor 25, for example, a gas chromatograph may be used. As the pressure sensor 27, a general use pressure sensor may be used. The output signals of these sensors 25 and 27 are input to the predictive control means 60.

A control valve 28 serving as the reflux ratio control means is attached to the reflux line 28. The opening degree of the control valve 28 is controlled by the output signal from the predictive control means 60 so as to control the reflux flow rate.

In the example shown in FIG. 2, a differential pressure sensor 30 is attached to the first extractive distillation tower 4 as a differential pressure detecting means for detecting the pressure difference between the inside of the top of the tower and the inside of the bottom of the tower. In this example, the top-bottom differential pressure data detected by the differential pressure sensor 30 is input to the predictive control means 60. Predictive control by the change of the pressure difference contributes only a little to the stability of the composition of the extract, but contributes a lot to the safety, so predictive control is preferable.

First and second impurity concentration sensors (impurity concentration detecting means) 32 and 34 for measuring the concentration of the trans-2-butene and cis-2-butene and other impurities present at the seventh stage are attached to the seventh stage from the bottom of the first extractive distillation tower 4. The first impurity concentration sensor 32 detects the concentration of the cis-2-butene, while the second impurity concentration sensor 34 measures the concentration of the trans-2-butene. These concentration sensors 32 and 34 are not particularly limited so long as they can detect the concentrations, but for example are comprised of gas chromatographs. The data on the concentrations detected by these concentration sensors 32 and 34 are input to the predictive control means 60.

Note that the positions of the first sensor and second sensor are not limited to the seventh stage from the bottom of the first extractive distillation tower 4. For example, they may be at the 7th stage from the bottom, on the stripped gas line 44 from the stripping tower 8, or at the condensate line 51 as well. While the concentration data will not match at these locations, there is a strong correlation in the amounts of change of the concentrations. If continuously measuring the concentrations at any of these locations, it is possible to accurately judge the concentrations at the other locations. Further, since the predictive control means uses the concentration data converted to data on the change of concentration, if the change in concentration at these locations can be accurately measured, accurate predictive control is possible.

A bottom heater 36 is provided as the bottom temperature control means at the bottom of the first extractive distillation tower 4. The bottom temperature is controlled based on the output signal corresponding to the data on the change of concentration from the predictive control means 60. The bottom temperature, as explained above, is generally held at 100 to 160° C., but in the present embodiment the bottom temperature is controlled based on the output signal from the predictive control means 60 in that temperature range. The heat source for the bottom heater 36 is not limited to steam. Hot water, a heat medium, etc. may also be mentioned. Of course, the bottom heater 36 can be controlled in temperature.

An extract containing a high concentration of butadiene present at the bottom of the tower 4 (containing solvent) is sent to the stripping tower 8 through line 38. At the stripping tower 8, as explained above, the solvent is separated from the extract and exhausted from the bottom. At the top of the stripping tower 8, stripped gas containing a large amount of butadiene from which the solvent has been separated is produced. This gas is sent from the top of the tower through a line 44 to the second extractive distillation tower 12 by a compressor 10. A return line 46 is connected to the line 44. The return line 46 is connected to a stage near the bottom of the first extractive distillation tower 4. The stripped gas containing a large amount of butadiene carried through the line 44 or its condensate is returned to the inside of the first extractive distillation tower The return line 46 is fitted with a return flowmeter 50 for detecting the flow rate in the line and a return flow rate control valve 48 for controlling the flow rate of the fluid flowing through the line. The control valve 48 is controlled in accordance with an output signal from the predictive control means 60 and controls the flow rate of the fluid returned inside the first extractive distillation tower 4 through the return line 46. The control valve 48 and the flowmeter 50 correspond to the return ratio control means. When returning part of the stripped gas to the first extractive distillation tower 4 as a gas, the remainder of the stripped gas is sent to the second extractive distillation tower 12 while controlling the value of the pressure sensor 52 by the control valve 56. When returning the condensate of the stripped gas to the first extractive distillation tower 4, the remainder of the condensate is sent to the second extractive distillation tower 12 while controlling the liquid level of a condensate drum by the control valve 56.

In the present invention, the predictive control means is not particularly limited, but as an example an explanation will be given of a method of control using the predictive control means 60 shown in FIG. 2 based on FIG. 3 and FIG. 4.

Figure 3:
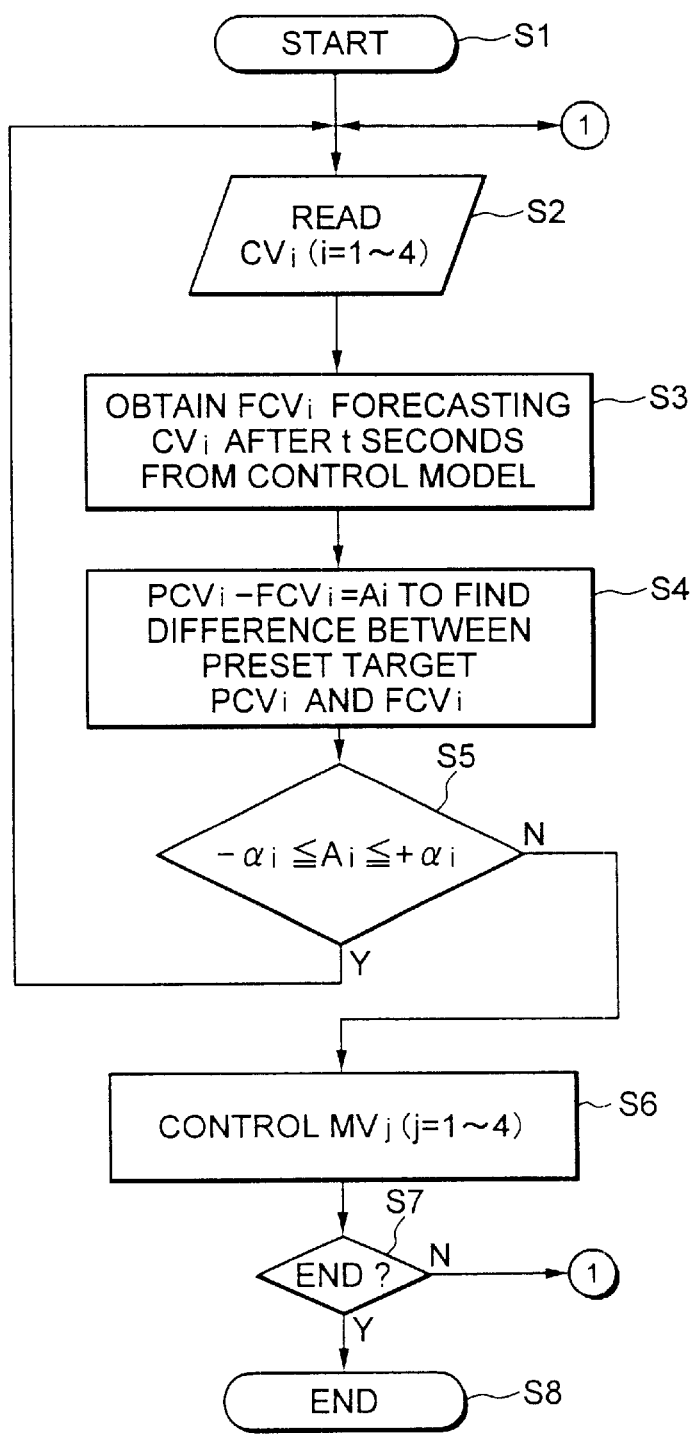
FIG. 3 is a flow chart of the method of control of a predictive control means shown in FIG. 2.

When the control starts at step S1 shown in FIG. 3, at step S2, the predictive control means 60 shown in FIG. 2 reads the data CVi (i=1 to 4). CV1 is the data of the concentration of the cis-2-butene detected by the impurity concentration sensor 32 at the seventh stage of the extractive distillation tower 2 shown in FIG. 2. CV2 is the data of the concentration of the trans-2-butene detected by the impurity concentration sensor 34 at the seventh stage of the extractive distillation tower 2 shown in FIG. 2. CV3 is the data of the concentration of the butadiene detected by the target material concentration sensor 25 attached to the top of the extractive distillation tower 2 shown in FIG. 2. CV4 is the top-bottom differential pressure data detected by the differential pressure sensor 30 of the extractive distillation tower 2 shown in FIG. 2. While not data essential for control as mentioned above, if this is used for control, the safety becomes higher, so use is preferred.

Next, at step S3 shown in FIG. 3, the data CV1 to CV4 after t seconds are forecast from a control model stored in the predictive control means 60 shown in FIG. 2 based on the data CV1 to CV4 and those values made FCV1 to FCV4. The control model stored in the predictive control means 60 is a control model determined based on the following formula. A model of the relation between the measurement data CV1 to CV4 in an actual first extractive distillation tower 4 and the control parameters (return ratio MV1, solvent ratio MV2, reflux ratio MV3, and bottom temperature MV4) is produced by this formula.

$$G_{ij}(S) = \frac{a_{ij}}{1 + b_{ij} \cdot S} e^{-c_{ij} \cdot s}$$

where, i=1 to 4 and
j=1 to 4

In the above formula, $G_{ij}$ shows the transfer function between CVi (i=1 to 4) and MVj (j=1 to 4), S is the parameter of a Laplace transform, and $a_{ij}$, $b_{ij}$, and $c_{ij}$ are values inherent to the processes corresponding to combinations of CVi (i=1 to 4) and MVj (j=1 to 4) and are found from the results of a step test. Note that a step test changes the MVj (j=1 to 4) in steps of any amount to find the response data of the CVi (i=1 to 4).

Using the control model established by this formula, at step S3 shown in FIG. 3, the data CV1 to CV4 after a predetermined time (t seconds) is forecast and the values used as FCV1 to FCV4. Note that "after t seconds" is not particularly limited, but is for example after 600 to 3600 seconds.

Next, at step S4 shown in FIG. 3, the difference Ai (i=1 to 4) between the target value PCVi preset for every data CV1 to CV4 and the forecasted value FCVi is calculated. Next, at step S5, it is confirmed if the difference Ai is in a predetermined range from -αi (minus allowable value) to +αi (plus allowable value). If the difference Ai is in the predetermined range, it means that the forecasted value FCVi of the CVi after t seconds is in the allowable range. Note that the allowable value αi is determined for each CVi. While not particularly limited, it is about 1 to 10 percent of the target value PCVi.

If all of the differences Ai are allowable values at step S5, the forecasted values FCVi of the CVi after t seconds are in the allowable range, so the control parameters MV1 to MV4 are maintained in their current states and the steps after step S2 are repeated. If even one of the differences Ai is outside of the allowable range at step S5, it means that the corresponding forecasted value FCVi is outside of the allowable range, so the routine proceeds to step S6, where the current settings of the control parameters MVi are changed so as to change the forecasted value FCVi deviating from the allowable range in a direction entering the allowable range. For example, when desiring to control a forecasted value FCVi deviating from the allowable range in a direction lowering the value, the current settings of the control parameters MVi are changed in the directions of the arrows shown in FIG. 4. In FIG. 4, the upward facing arrows mean raising the current settings of the control parameters MVi.

For example, when the forecasted concentration value FCV1 of the seventh stage cis-2-butene corresponding to the data CVI detected by the concentration sensor 32 shown in FIG. 2 rises out of the predetermined range, the forecasted concentration value FCV1 of the seventh plate cis-2-butene is lowered by changing the current settings of the control parameters MVi as follows: That is, the predictive control means 60 shown in FIG. 2 is used to operate the control valve 48 to increase the return ratio MV1 to the first extractive distillation tower 2 through the return line 46. Further, the predictive control means 60 shown in FIG. 2 is used to control the control valve 23 to reduce the ratio of the solvent MV2 fed to the first extractive distillation tower 4 through the solvent feed line 22. Further, the predictive control means 60 shown in FIG. 2 is used to control the control valve 28 of the reflux line 26 to reduce the reflux ratio MV3. Further, the predictive control means 60 shown in FIG. 2 is used to control the heater 36 to increase the bottom temperature MV4.

Similarly, when the forecasted value of the concentration FCV2 of the seventh-stage trans-2-butene corresponding to the data CV2 detected by the concentration sensor 34 shown in FIG. 2 rises outside of the predetermined range, the FCV2 is lowered by changing the current settings of the control parameters MVi in accordance with the directions of the arrows shown in FIG. 4. Similarly, when the forecasted value of the concentration FCV3 of the butadiene at the top of the tower corresponding to the data CV3 detected by the concentration sensor 25 shown in FIG. 2 rises outside of the predetermined range, the FCV3 is lowered by changing the current settings of the control parameters MVi in accordance with the directions of the arrows shown in FIG. 4. When the forecasted top-bottom differential pressure value FCV4 corresponding to the data CV4 detected by the differential pressure sensor 30 shown in FIG. 2 rises outside of the predetermined range, it is preferable in terms of safety to lower this FCV4 by changing the current settings of the control parameters MVi in accordance with the directions of the arrows shown in FIG. 4. Note that when the forecasted values FCV1 to FCV4 corresponding to the data CV1 to CV4 drop outside of the predetermined ranges, the control parameters MVi are controlled by the predictive control means 60 in directions opposite to the arrows shown in FIG. 4.

By using the method of control of the first extractive distillation tower 4 according to the present embodiment, it is possible to reduce the variation in the concentration CV1 of the seventh stage cis-2-butene to about 0.63 percent (min. 8.50–max. 9.13%). Note that in conventional control, the variation in the concentration of the seventh stage cis-2-butene was 1.29 percent (min. 7.79–max. 9.08%). Further, according to the method of the present embodiment, it is possible to reduce the variation in the concentration CV2 of the seventh stage trans-2-butene to about 0.32 percent (min. 1.35–max. 1.67%). Note that in conventional control, the variation in the concentration CV2 of the seventh stage trans-2-butene was 0.54 percent (min. 1.28–max. 1.82%). Further, according to the method of the present embodiment, the variation in the concentration CV3 of the butadiene at the top of the tower can be reduced to about 0.21 percent (min. 0.19–max. 0.40%). Note that in conventional control, the variation in the concentration CV3 of the butadiene at the top of the tower was 0.29 percent (min. 0.13% –max. 0.42%).

According to the apparatus and method of the present embodiment, by suppressing the variations of the concentrations CV1 and CV2 of the cis-2-butene and trans-2-butene as impurities near the bottom of the first extractive distillation tower 4 and suppressing the variations of the concentration of the butadiene at the top of the tower, it is possible to stabilize the concentration of butadiene included in the extract taken out from the bottom. As a result, increasing the purity of the conjugated butadienes in the subsequent process becomes easy, and high purity conjugated butadienes can be stably obtained.

Second Embodiment

In the present embodiment, the process of separation and purification of unsaturated hydrocarbons other than conjugated dienes will be explained. In the present embodiment, the raffinate C4R produced as a byproduct in the process of separation and purification of the conjugated dienes from the $C_4$ fraction or the $C_5$ fraction of the first embodiment shown in FIG. 1 (residual gas of feedstock C4F from which butadiene has been separated) is used as the feedstock and butenes are separated and purified.

Figure 5:
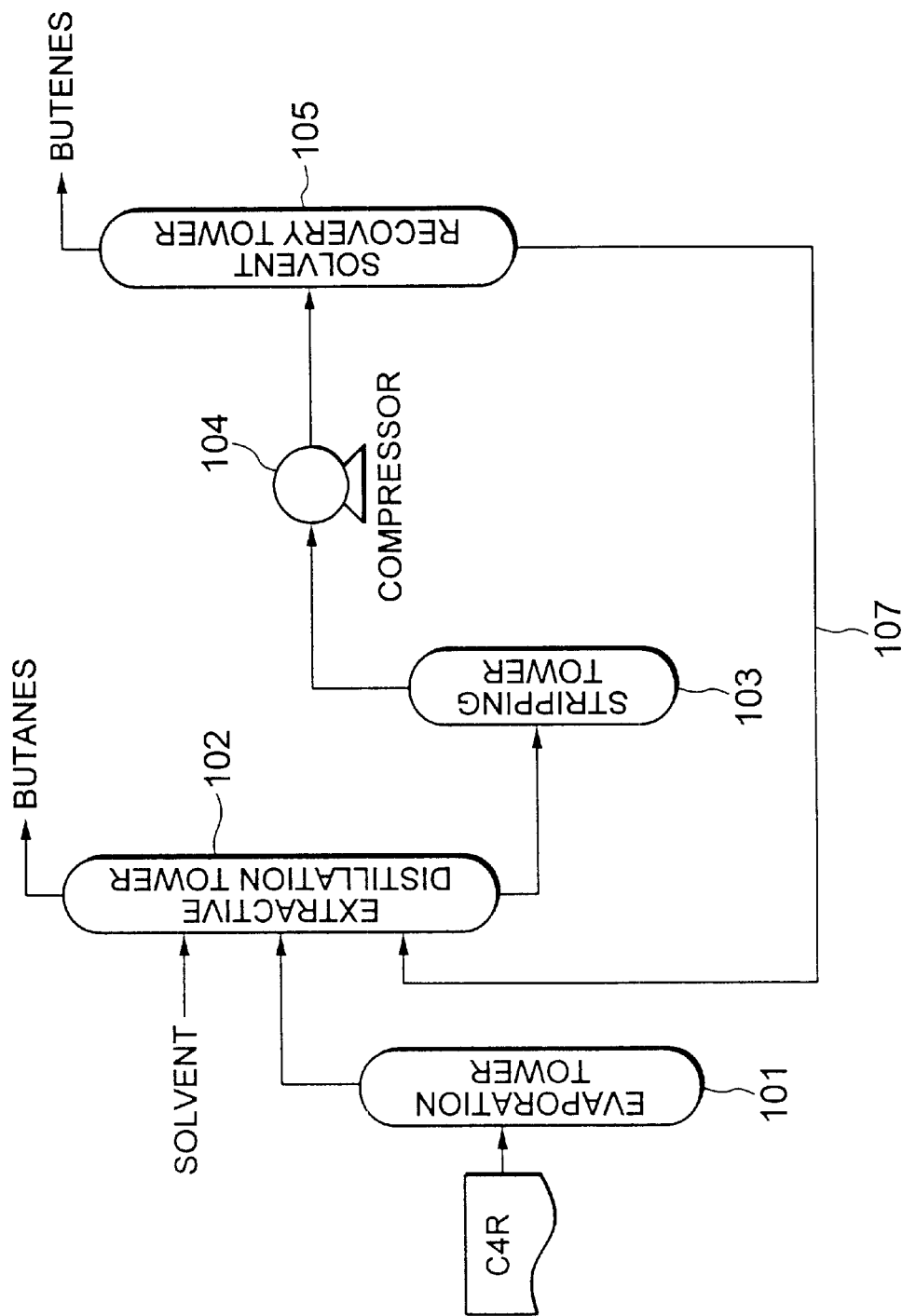
FIG. 5 is a schematic view of the overall configuration of a separation and purification apparatus for butenes.

The raffinate C4R contains 30 to 80 percent butenes. The rest consists of butanes. As shown in FIG. 5, the residual gas BBR is fed to the evaporation tower 101 where it is vaporized and then is fed to the extractive distillation tower 102.

Further, a solvent is fed to a stage higher than the position of feeding the BBR of the first extractive distillation tower 102. The solvent containing the butenes is taken out from the bottom of the extractive distillation tower 102. Almost all of the butanes contained in the BBR are exhausted from the top of the tower. The solvent containing the butenes taken out from the bottom of the extractive distillation tower 102 is fed to a position several stages lower than the top of a stripping tower 103. In the stripping tower, the butenes and solvent are separated.

The bottom temperature of the extractive distillation tower 102 is controlled to become the boiling point of the solvent at the tower pressure, that is, normally 0.5 to 5 atm. Butenes are taken out from the top of the stripping tower 103. Part is sent to the solvent recovery tower 105, while the remainder is returned to the extractive distillation tower 102. Normally solvent of 100 to 200° C. is taken out from the bottom of the stripping tower 103. At the solvent recovery tower 105, butenes are recovered from the top of the tower, while a mixture of the solvent and butenes is returned from the bottom of the tower to the bottom of the extractive distillation tower 102. The butenes recovered from the tower 105 are generally a mixture of n-butene, isobutene, 1-butene, and 2-butene. When separation and purification of these are necessary, since almost all of the butanes hard to be separated and purified are removed, separation and purification can be easily performed by a normal distillation operation.

In the present embodiment, by detecting the change in the concentration of the impurities near the bottom of the extractive distillation tower 102 and the change of the concentration of the butenes in the butane gas discharged from the top of the extractive distillation tower 102 and controlling the ratio of the solvent fed to the extractive distillation tower 102, controlling the return ratio from the stripping tower 103 through the solvent recovery tower 105 to the extractive distillation tower 102 controlling the reflux ratio at the top of the extractive distillation tower 102, and controlling the bottom temperature of the extractive distillation tower 102 in accordance with these changes, it is possible to extract a constant concentration of butenes. In the present embodiment, the concentration of butenes in the finally obtained extract is at least 99 percent.

The control apparatus and control method of the extractive distillation tower 102 according to the present embodiment is similar to the case of the first extractive distillation tower 4 shown in FIG. 2 except that the feedstock fed is changed from BBF to BBR, the gas exhausted from the top of the tower is changed from BBR to a gas containing butenes, the impurities detected as CV1 and CV2 are changed from cis-2-butene and trans-2-butene to n-butane and other butanes, and the extract taken out from the bottom of the extractive distillation tower 102 is changed from conjugated dienes to butenes. The common description will be omitted.

According to the apparatus and method of the present embodiment, by suppressing the variations of the concentrations CV1 and CV2 of the butane impurities near the bottom of the extractive distillation tower 102 and suppressing the variations of the concentration of the butenes at the top of the tower, it is possible to stabilize the concentration of butenes included in the extract taken out from the bottom. As a result, increasing the purity of the butenes in the subsequent process becomes easy, the loss of the butenes at the top of the tower can be suppressed, and high purity butenes can be stably obtained.

Other Embodiments

Note that the present invention is not limited to the above embodiments and may be modified in various ways within the scope of the invention.

For example, in the first embodiment, two impurity concentration sensors 32 and 34 were used as the impurity concentration detecting means in the first extractive distillation tower 4, but in the present invention it is also possible to use either of the impurity concentration sensors 32 or 34 and omit the other one. This because there is a correlation between the concentration of the cis-2-butene and the concentration of the trans-2-butene detected by these concentration sensors 32 and 34 and by detecting and suppressing the concentration of either of these, it is possible to also suppress fluctuations in concentration of the other. If omitting one, however, it is preferable to omit the impurity concentration sensor 32 for detecting the concentration of the cis-2-butene. This is because the cis-2-butene can be removed in a process after the first extractive distillation tower 4. Note that the same applies to the second embodiment.

Further, in the first embodiment, the concentration of the target butadiene was detected at the top of the extractive distillation tower 4, but in the present invention the location is not limited to the top of the tower. Another location is also possible. However, detection at the top of the tower is most preferable. The same applies to the second embodiment.

What is claimed is:

1. A separation and purification apparatus for an unsaturated hydrocarbon comprising;
    an extractive distillation tower supplied with feedstock containing unsaturated hydrocarbon and a solvent for distilling the feedstock to separate and purify a target unsaturated hydrocarbon;
    an impurity concentration detecting means for detecting a concentration of a specific impurity other than the target unsaturated hydrocarbon at the extractive distillation tower or another tower connected to the extractive distillation tower;
    a target unsaturated hydrocarbon concentration detecting means for detecting a concentration of the target unsaturated hydrocarbon at the extractive distillation tower or another tower connected to the extractive distillation tower;
    a return ratio control means for controlling a flow rate of part of a fluid including the target unsaturated hydrocarbon taken out from a bottom of the extractive distillation tower and returned to the extractive distillation tower;
    a solvent flow control means for controlling a flow rate of the solvent fed to the extractive distillation tower;
    a reflux ratio control means for controlling a flow rate or part of a residual component of the feed stock taken out from a top of the extractive distillation tower and refluxed to the extractive distillation tower,
    a bottom temperature control means for controlling a bottom temperature of the extractive distillation tower; and
    a predictive control means for calculating forecasted values of the concentration of the specific impurity and the concentration of the target unsaturated hydrocarbon based on values detected by the impurity concentration detecting means and target unsaturated hydrocarbon concentration detecting means and controlling the return ratio control means, solvent ratio control means, reflux ratio control means, and bottom temperature control means based on the forecasted values.

2. The separation and purification apparatus for an unsaturated hydrocarbon as set forth in claim 1,
    further comprising a differential pressure detecting means for detecting a differential pressure between a top and bottom of said extractive distillation tower,
    wherein the predictive control means further calculates forecasted values of the concentration of the specific impurity and the concentration of the target unsaturated hydrocarbon based on values detected by the impurity concentration detecting means, target unsaturated hydrocarbon concentration detecting means, and differential pressure detecting means and controls the return ratio control means, solvent ratio control means, reflux ratio control means, and bottom temperature control means based on the forecasted values.

3. The separation and purification apparatus for an unsaturated hydrocarbon as set forth in claim 1 or 2, wherein a solvent feeding means for feeding said solvent to said extractive distillation tower is provided at a position higher than a petroleum fraction feed means for feeding a petroleum fraction containing said unsaturated hydrocarbon.

4. The separation and purification apparatus for an unsaturated hydrocarbon as set forth in claims 1 or 2, further comprising an evaporation tower for vaporizing a petroleum fraction containing said unsaturated hydrocarbon before being fed to said extractive distillation tower.

5. The separation and purification apparatus for an unsaturated hydrocarbon as set forth in claims 1 or 2, further comprising a stripping tower fed with a fluid containing the target unsaturated hydrocarbon taken out from the bottom of said extractive distillation tower and separating the unsaturated hydrocarbon and solvent.

6. A method for separation and purification of an unsaturated hydrocarbon comprising the steps of:
    supplying a feedstock containing a target unsaturated hydrocarbon and a solvent to an extractive distillation tower;
    detecting a concentration of a specific impurity other than the target unsaturated hydrocarbon at the extractive distillation tower or another tower connected to the extractive distillation tower;
    detecting a concentration of the target unsaturated hydrocarbon at the extractive distillation tower or another tower connected to the extractive distillation tower;
    controlling a return flow rate of part of a fluid containing the target unsaturated hydrocarbon taken out from a bottom of the extractive distillation tower and returned to the extractive distillation tower;
    controlling a flow rate of the solvent fed to said extractive distillation tower;
    controlling a reflux flow rate of part of a residual component of the feedstock taken out from a top of the extractive distillation tower and refluxed to the extractive distillation tower;
    controlling a bottom temperature of the extractive distillation tower; and
    calculating forecasted values of the concentration of the target unsaturated hydrocarbon based on values detected by the impurity concentration detecting step and target material concentration detecting step and controlling the return flow rate, the flow rate of the solvent, the reflux flow rate, and the bottom temperature based on the forecasted values.

7. The method of separation and purification of an unsaturated hydrocarbon as set forth in claim 6,
    further comprising detecting a differential pressure between a top and bottom of said extractive distillation tower and
    calculating forecasted values of the concentration of the specific impurity and the concentration of the specific impurity and the concentration of the target unsaturated hydrocarbon based on values detected by the impurity concentration detecting step, target material concentration detecting step, and differential pressure detecting step.

8. The method of separation and purification of an unsaturated hydrocarbon as set forth in claim 6 or 7, further comprising feeding said solvent to said extractive distillation tower from a position higher than a petroleum fraction feed means for feeding a petroleum fraction containing said unsaturated hydrocarbon.

9. The method of separation and purification of an unsaturated hydrocarbon as set forth in claims 6 or 7, further comprising vaporizing a petroleum fraction containing said unsaturated hydrocarbon before being fed to said extractive distillation tower and then feeding the petroleum fraction to said extractive distillation tower.

10. The method of separation and purification as set forth in claims 6 or 7, further comprising separating a fluid containing the target unsaturated hydrocarbon taken out from the bottom of said extractive distillation tower into the unsaturated hydrocarbon and solvent.

11. The method of separation and purification as set forth in claims 6 or 7, further comprising using a petroleum fraction containing a conjugated diene as a petroleum fraction containing the unsaturated hydrocarbon before being fed to the extractive distillation tower.

12. The method of separation and purification as set forth in claim 11, wherein said conjugated diene is butadiene and the concentration of said specific impurity is the concentration of cis-2-butene and/or the concentration of trans-2-butene.

13. The method of separation and purification as set forth in claims 6 or 7, further comprising controlling the bottom temperature of said extractive distillation tower to become the boiling point of the solvent at the tower pressure.

14. The method of separation and purification as set forth in claims 6 or 7, further comprising detecting the concentration of said target unsaturated hydrocarbon at a top of said extractive distillation tower.

* * * * *